(12) United States Patent
Goldish et al.

(10) Patent No.: US 11,654,311 B2
(45) Date of Patent: May 23, 2023

(54) TRUNK CONTROL SYSTEMS AND WHEELCHAIRS COMPRISING SAME

(71) Applicants: United States Government as Represented by the Department of Veterans Affairs, Washington, DC (US); Fraunhofer-Gesellschaft zur Foerdrung der angewandten Forschung e. V., Munich (DE)

(72) Inventors: Gary Goldish, Minneapolis, MN (US); Andrew Hansen, Minneapolis, MN (US); Stuart R. Fairhurst, Minneapolis, MN (US); Gregory O. Voss, Apple Valley, MN (US); Urs Schneider, Munich (DE)

(73) Assignees: United States Government As Represented By The Department Of Veterans Affairs, Washington, DC (US); Fraunhofer-Gesellschaft zur Foerderung der angewandten Forschung e. V., Munich (DE)

( * ) Notice: Subject to any disclaimer, the term of this patent is extended or adjusted under 35 U.S.C. 154(b) by 420 days.

(21) Appl. No.: 16/848,303

(22) Filed: Apr. 14, 2020

(65) Prior Publication Data

US 2020/0324152 A1    Oct. 15, 2020

Related U.S. Application Data

(60) Provisional application No. 62/833,990, filed on Apr. 15, 2019.

(51) Int. Cl.
*A61G 5/10*    (2006.01)
*A62B 35/00*   (2006.01)
(Continued)

(52) U.S. Cl.
CPC ........ *A62B 35/0012* (2013.01); *A61F 5/3792* (2013.01); *A61G 5/10* (2013.01); *A62B 35/0075* (2013.01); *B60N 2/245* (2013.01)

(58) Field of Classification Search
CPC ............... B60N 2/245; A62B 35/0012; A62B 35/0075; A61F 5/3792; A61G 5/10
See application file for complete search history.

(56) References Cited

U.S. PATENT DOCUMENTS 3,761,126 A    9/1973  Mulholland
4,170,991 A *  10/1979 Kella ...................... A61G 5/10
                                                         128/845

(Continued)

FOREIGN PATENT DOCUMENTS

WO    WO 2007/090677 A1    8/2007

OTHER PUBLICATIONS

International Search Report and Written Opinion for PCT/US/2020/028078, dated Jul. 24, 2020.

*Primary Examiner* — Philip F Gabler
(74) *Attorney, Agent, or Firm* — Ballard Spahr LLP

(57) ABSTRACT

A trunk control system having a harness assembly and a flexion control assembly. The harness assembly has a backrest member and a harness secured to the backrest member. The backrest member is configured to be moveably coupled to a wheelchair. The backrest member is selectively moveable about and between a fully retracted position and a fully extended position. The harness cooperates with the backrest member to define a receiving space for receiving at least a portion of a torso of a wheelchair user. The flexion control assembly is coupled to the backrest member of the harness assembly. The flexion control assembly is configured to (Continued)

selectively permit or restrict movement of the backrest member about and between the fully retracted position and the fully extended position.

32 Claims, 12 Drawing Sheets

(51) Int. Cl.
*B60N 2/24* (2006.01)
*A61F 5/37* (2006.01)

(56) References Cited

U.S. PATENT DOCUMENTS

| | | | |
|---|---|---|---|
| 4,177,807 A * | 12/1979 | Ocel | A61G 5/10 |
| | | | D29/101.1 |
| 4,530,122 A | 7/1985 | Sanders et al. | |
| 5,074,588 A | 12/1991 | Huspen | |
| 5,165,123 A | 11/1992 | Colpron | |
| 5,395,158 A | 3/1995 | Cordia | |
| 5,601,527 A | 2/1997 | Selkowitz | |
| 6,213,558 B1 | 4/2001 | Axelson et al. | |
| 8,007,046 B2 * | 8/2011 | Rothschild | B64D 11/06 |
| | | | 297/485 |
| 9,233,036 B1 | 1/2016 | Frederick et al. | |
| 9,694,717 B2 | 7/2017 | Hyde et al. | |
| 11,065,143 B2 * | 7/2021 | Torres | A61F 5/3792 |
| 2007/0182570 A1 | 8/2007 | Overturf | |
| 2011/0254344 A1 | 10/2011 | Freeman et al. | |

* cited by examiner

TRUNK CONTROL SYSTEMS AND WHEELCHAIRS COMPRISING SAME

CROSS-REFERENCE TO RELATED APPLICATION

This application claims priority to and the benefit of the filing date of U.S. Provisional Patent Application No. 62/833,990, filed Apr. 15, 2019, which is incorporated herein by reference in its entirety.

FIELD

The disclosed invention relates to a trunk control system that permits controlled movement of the torso of a wheelchair user relative to the wheelchair. Wheelchairs incorporating such trunk control systems are also disclosed.

BACKGROUND

Over 280,000 people living in the United States have a spinal cord injury (SCI), with approximately 17,000 new injuries every year. One of the significant challenges those individuals face is living and working with limited or no control of their torso or "trunk." This lack of trunk control significantly impacts their ability to carry out a broad range of simple daily tasks. Yet no commercially available solutions exist that allow some degree of movement, while also providing trunk support.

It is known that persons with SCI between C5-T8 have reduced control of their trunk muscles, and represent about 56% of the overall SCI population (Stover et al, 1995). It is also known that trunk control is essential for many activities of daily living (Gabison et al, 2014). Some persons with trunk control deficiencies use a seat belt at the chest level to assist with trunk posture in the wheelchair, which keeps them in a vertical seated posture. This vertical seated posture restrains their functional reach with both hands (bimanual workspace), does not allow forward leaning to relieve pressure on the seated area (e.g., the ischial tuberosities and the sacrum), and does not allow the person to lean forward when using their wheelchairs on an inclined surface to keep the center of mass within the base of support of the wheelchair.

Some persons with trunk control deficiencies choose not to use a seat belt and instead control their trunk using one or both arms to manually move and hold the upper body from falling. These persons can also have fully flexed trunk postures (i.e., chest on knees) that occur as a result of gravity or vertical postures in the wheelchair, but cannot work with postures between these two extremes without using one or both arms to hold their position. These two extremes dramatically limit the available workspace for bimanual tasks. Some wheelchair users use chest straps to assist with trunk posture, but acceptance is limited because a tight chest strap connected to a rigid backrest can be considered a form of restraint.

A current approach for the improvement of trunk control is the use of implanted electrodes in the hip and back extensor muscles (Murphy et al, 2014; Audu et al, 2015; Crawford et al, 2017) that can be controlled to extend the trunk using functional neuromuscular stimulation (FNS). While initial results of this approach are promising, it requires a surgery that not all persons with SCI are interested in having. Thus, other solutions are needed.

Accordingly, there is a need for improved trunk control systems that are less restraining and that do not require surgery.

SUMMARY

Described herein, in various aspects, is a trunk control system having a harness assembly and a flexion control assembly. The harness assembly can have a backrest member and a harness secured to the backrest member. The backrest member can be moveably coupled to a wheelchair. In use, the backrest member can be selectively moveable about and between a fully retracted position and a fully extended position. The harness can cooperate with the backrest member to define a receiving space for receiving at least a portion of a torso of a wheelchair user. The flexion control assembly can be coupled to the backrest member of the harness assembly, and the flexion control assembly can be configured to selectively permit or restrict movement of the backrest member about and between the fully retracted position and the fully extended position.

Optionally, the flexion control assembly can include a tensioning component, such as a rope, a cable, a cord, a strap, and the like. The tensioning component can be secured to the backrest member and wound around a spool. A motor can be operatively coupled to the spool and configured to effect movement of the spool to selectively release or retract the tensioning component on the spool. A controller can be operatively coupled to the motor, and a user input device can be communicatively coupled to the controller. The controller can be configured to receive an instruction from the user input device that is indicative of a desired movement of the backrest member, and the controller can be configured to cause the motor to move the spool to achieve the desired movement of the backrest member.

Wheelchairs including trunk control systems and methods of using such wheelchairs and trunk control systems are also described.

Additional advantages of the invention will be set forth in part in the description that follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION OF THE DRAWINGS

These and other features of the preferred embodiments of the invention will become more apparent in the detailed description in which reference is made to the appended drawings wherein:

As shown in FIG. 1B, the hands of the user do not reach substantially beyond the anterior location of the feet.

As shown in FIG. 2C, in an extended position, the hands of the user can now reach beyond the anterior location of his feet.

As shown in FIGS. 5A-5B, the tensioning component passes through the outer housing and onto a spool that is connected to an electric motor.

DETAILED DESCRIPTION

Figure 1A:
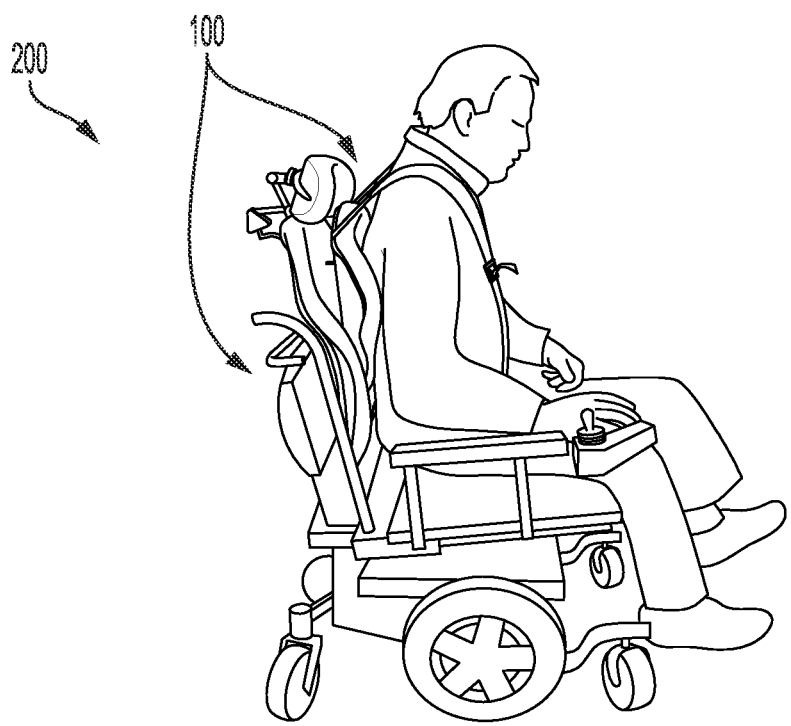
FIGS. 1A-1B depict a harness assembly in a fully retracted position in which a trunk control system as disclosed herein holds a user in place, but limits functional reach.
Figure 1B:
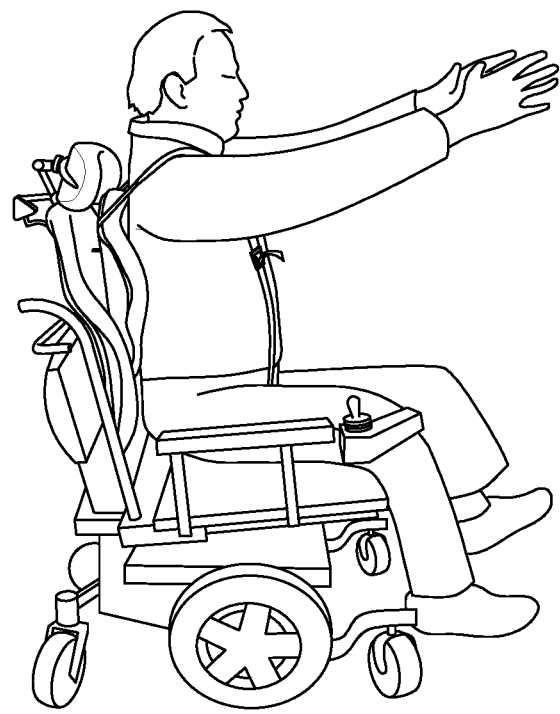
Figure 2A:
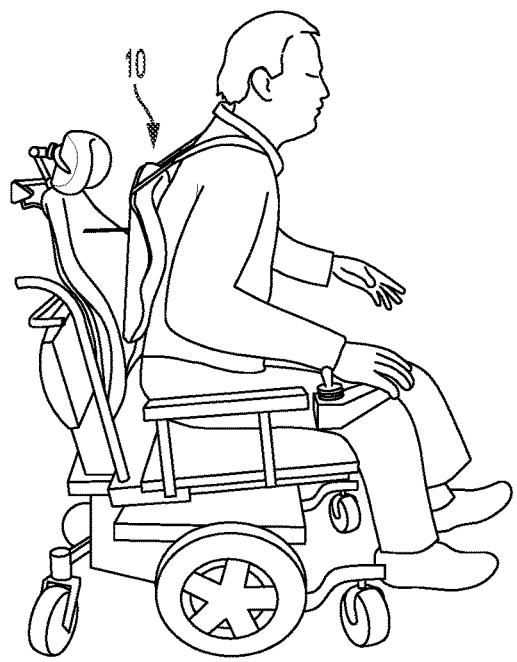
FIGS. 2A-2C depict progressive trunk fluxion as a user controls the trunk control system as disclosed herein, thereby extending his functional reach.
Figure 2B:
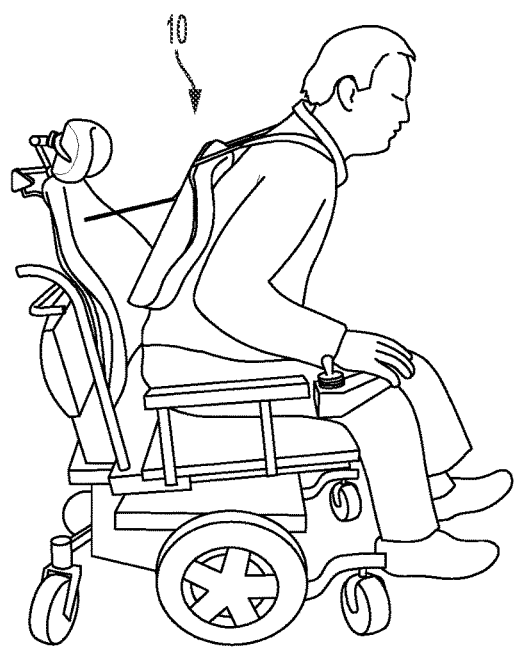
Figure 2C:
Figure 3A:
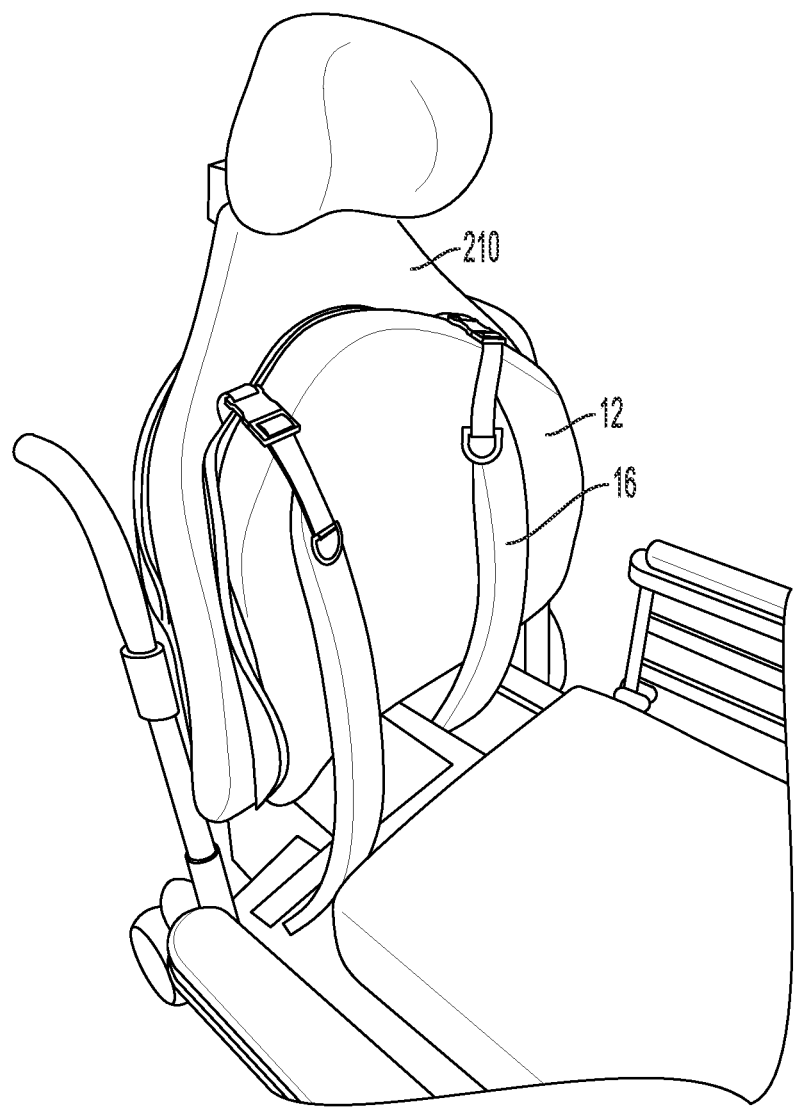
FIG. 3A is an image providing a front perspective view of a harness assembly as disclosed herein.
Figure 3B:
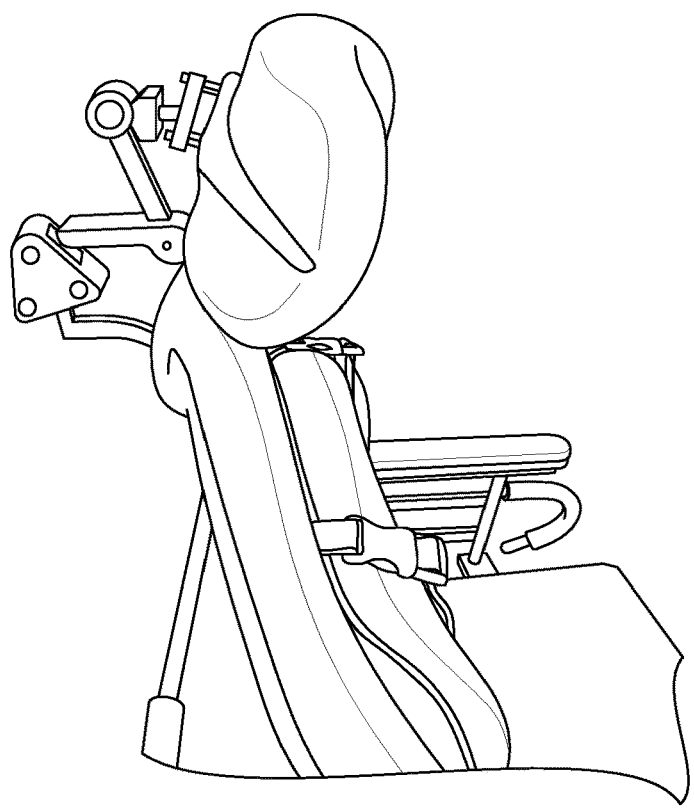
FIG. 3B is an image providing a side view of the harness assembly of FIG. 3A, along with a back support portion of a seat of a wheelchair.
Figure 3C:
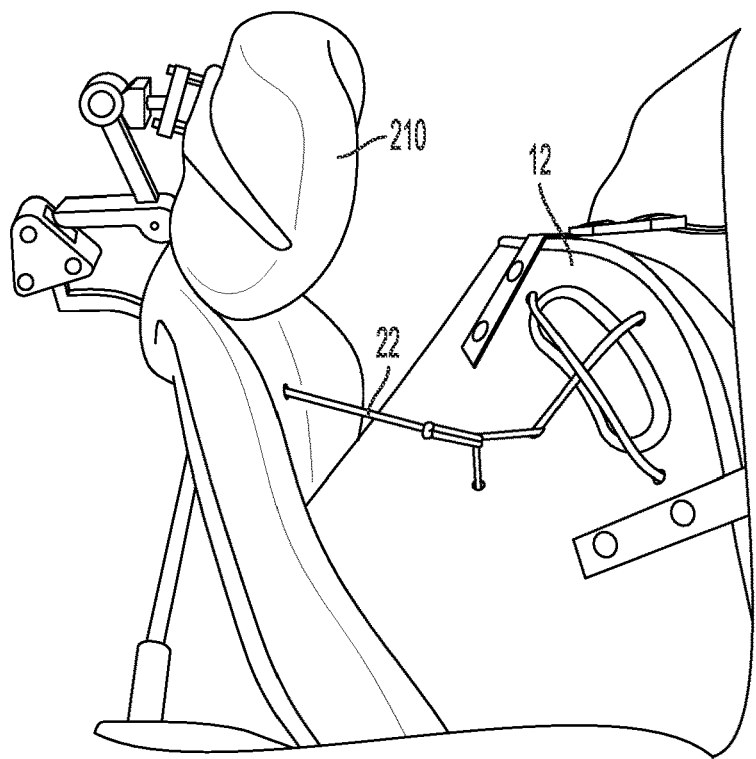
FIG. 3C is an image providing a side view of the harness assembly during trunk flexion. As shown, a tensioning component (e.g., a Bowden cable) can be connected to the harness assembly and extend through the seat of the wheelchair).
Figure 4A:
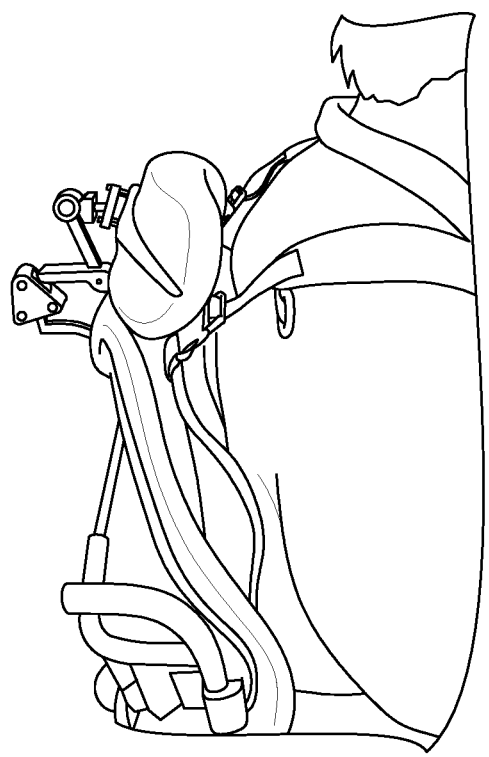
FIG. 4A is an image providing a top perspective view of a harness assembly in a fully retracted position as disclosed herein.
Figure 4B:
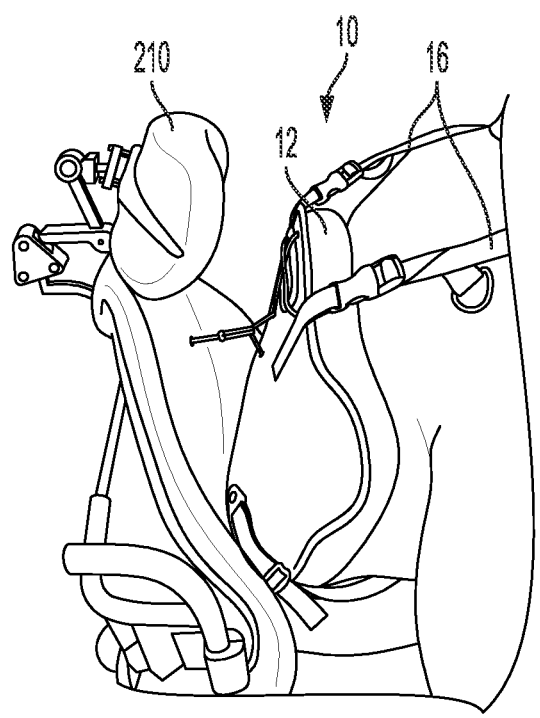
FIG. 4B is an image showing the extension of a tensioning component, allowing forward movement of the harness assembly and trunk flexion of the wheelchair user.
Figure 4C:
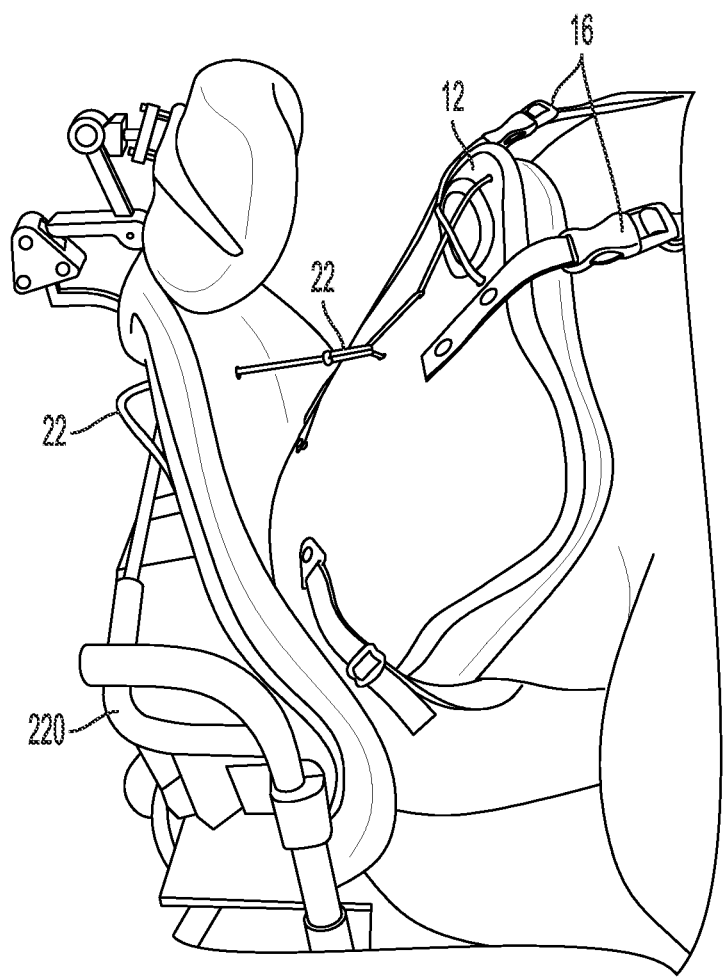
FIG. 4C is an image showing a side view of the harness assembly and the tensioning component with the trunk in a flexed position.
Figure 5A:
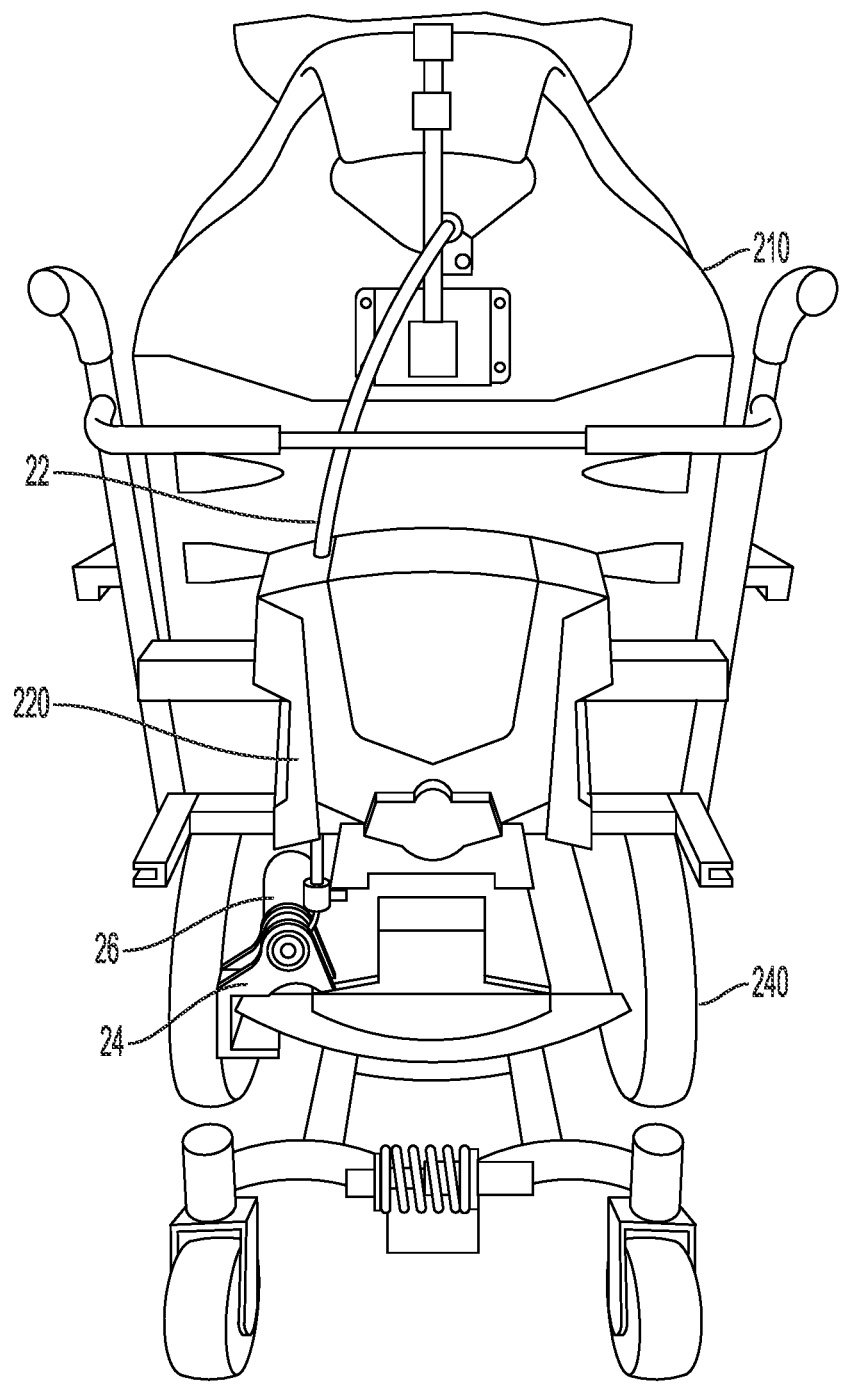
FIG. 5A is an image providing a rear view of a wheelchair having an outer housing for receiving a portion of a tensioning component (e.g., a Bowden cable) as disclosed herein. As shown, the outer housing can be mounted on the top end to the backrest of the wheelchair seat.
Figure 5B:
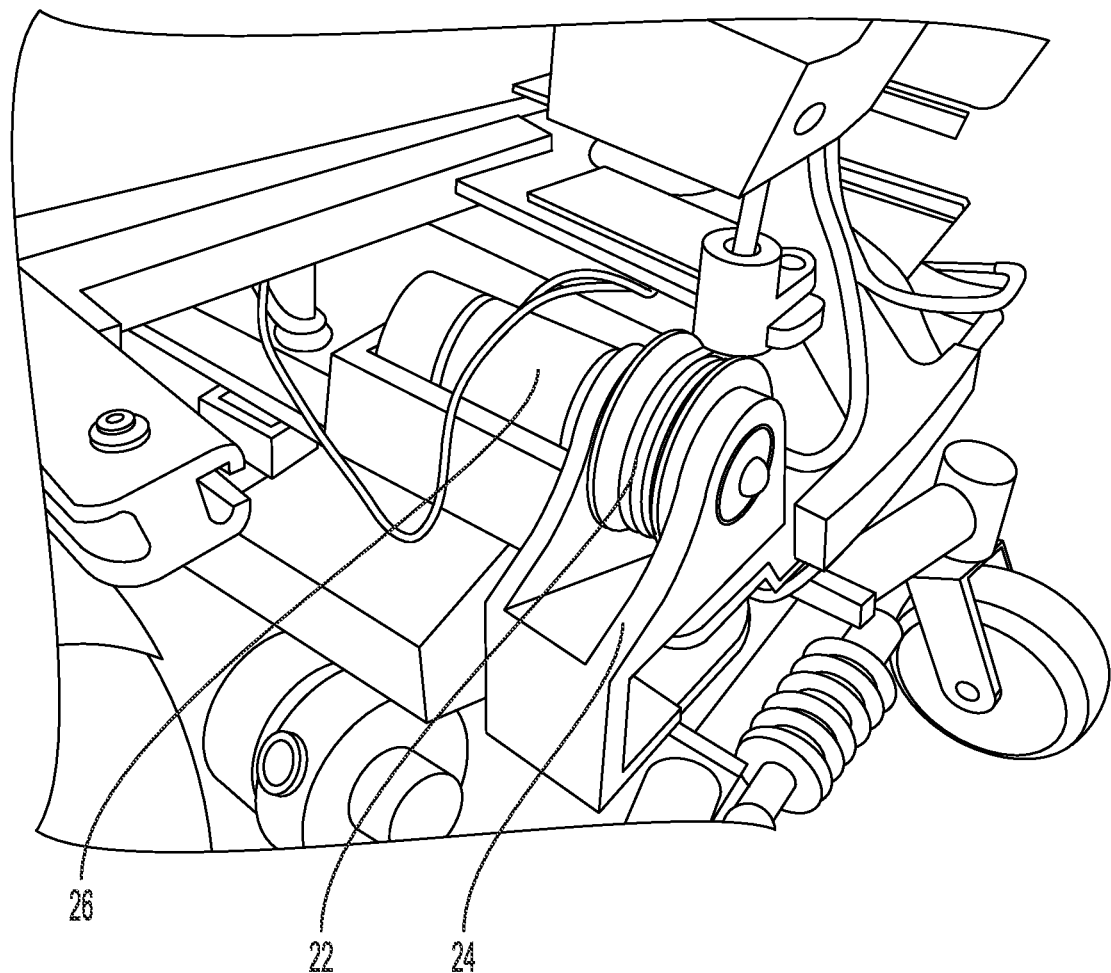
As shown in FIG. 5B, the outer housing can be secured or mounted on its bottom end to a frame surface of the powered wheelchair.

The present invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout. It is to be understood that this invention is not limited to the particular methodology and protocols described, as such may vary. It is also to be understood that the terminology used herein is for the purpose of describing particular embodiments only, and is not intended to limit the scope of the present invention.

Many modifications and other embodiments of the invention set forth herein will come to mind to one skilled in the art to which the invention pertains having the benefit of the teachings presented in the foregoing description and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

As used herein the singular forms "a," "an," and "the" include plural referents unless the context clearly dictates otherwise. For example, use of the term "a controller" can refer to one or more of such controllers, and so forth.

All technical and scientific terms used herein have the same meaning as commonly understood to one of ordinary skill in the art to which this invention belongs unless clearly indicated otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. Optionally, in some aspects, when values are approximated by use of the antecedent "about," it is contemplated that values within up to 15%, up to 10%, up to 5%, or up to 1% (above or below) of the particularly stated value can be included within the scope of those aspects. Similarly, in some optional aspects, when values are approximated by use of the terms "substantially" or "generally," it is contemplated that values within up to 15%, up to 10%, up to 5%, or up to 1% (above or below) of the particular value can be included within the scope of those aspects. When used with respect to an identified property or circumstance, "substantially" or "generally" can refer to a degree of deviation that is sufficiently small so as to not measurably detract from the identified property or circumstance, and the exact degree of deviation allowable may in some cases depend on the specific context.

As used herein, the terms "optional" or "optionally" mean that the subsequently described event or circumstance may or may not occur, and that the description includes instances where said event or circumstance occurs and instances where it does not.

As used herein, the term "at least one of" is intended to be synonymous with "one or more of." For example, "at least one of A, B and C" explicitly includes only A, only B, only C, and combinations of each.

The word "or" as used herein means any one member of a particular list and also includes any combination of members of that list.

It is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including: matters of logic with respect to arrangement of steps or operational flow; plain meaning derived from grammatical organization or punctuation; and the number or type of aspects described in the specification.

The following description supplies specific details in order to provide a thorough understanding. Nevertheless, the skilled artisan would understand that the apparatus, system, and associated methods of using the apparatus can be implemented and used without employing these specific details. Indeed, the apparatus, system, and associated methods can be placed into practice by modifying the illustrated apparatus, system, and associated methods and can be used in conjunction with any other apparatus and techniques conventionally used in the industry.

As described in more detail below, disclosed herein is a trunk control system having a harness that is worn by a wheelchair user. In a fully retracted position, the harness holds the user against the seat back of the wheelchair. However, the user is able to allow flexion of his or her trunk using a user input device (e.g., a joystick on the powered wheelchair) to slowly release a tensioning component, such as a rope, a cable, a cord, a strap, or the like. When the user has reached a desired trunk flexion, the trunk control system can be configured to hold the trunk from falling forward via tension in the tensioning component, thereby providing the user with the ability to reach further in the anterior direction. To return, the user can input instructions through the user input device (optionally, using the posterior of their elbow to push the joystick backward), thereby controlling the system to pull the user back to a vertical posture.

More generally, described herein is a trunk control system having a harness configured to be worn by a wheelchair user. One or more tensioning components (e.g., ropes) can be attached to a posterior portion of the harness and configured to be selectively released or retracted to adjust a position of the harness. The system can further comprise means for controlling a path of the one or more tensioning components. The system can still further comprise means for releasing or retracting the one or more tensioning components. Still further, the system can comprise means for controlling the release or retraction of the one or more tensioning components.

Disclosed herein, in various aspects and with reference to FIGS. 1A-7B, is a trunk control system 100 comprising a harness assembly 10 and a flexion control assembly 20. The harness assembly 10 can have a backrest member 12 and a harness 14 secured to the backrest member. The backrest member 12 can be configured to be moveably coupled to a wheelchair 200. As shown in FIGS. 1A-2C and 4A-4C, the backrest member 12 can be selectively moveable about and between a fully retracted position (FIGS. 1A-1B) and a fully extended position (FIG. 2C). Optionally, the fully retracted position can correspond to a substantially vertical orientation. In exemplary aspects, it is contemplated that the fully retracted position can correspond to a vertical or slightly reclined position. From the fully retracted position, it is contemplated that the trunk can be selectively flexed from about 5 up to about 85 degrees (relative to the fully retracted position) toward the fully extended position. The harness 14 can cooperate with the backrest member 12 to define a receiving space 15 for receiving at least a portion of a torso of a wheelchair user. Optionally, as shown in FIGS. 3A and 4A-4C, the harness 14 can comprise first and second shoulder straps 16. In further aspects, it is contemplated that the harness 14 can further comprise a releasable horizontal strap that is configured to extend across a chest of the wheelchair user in between the first and second shoulder straps 16.

In exemplary aspects, as shown in FIGS. 3A-4C, the flexion control assembly 20 can be coupled to the backrest member 12 of the harness assembly 10. In these aspects, the flexion control assembly 20 can be configured to selectively permit or restrict movement of the backrest member 12 about and between the fully retracted position and the fully extended position. Optionally, it is contemplated that the backrest member 12 can be a rigid or substantially rigid structure. It is further contemplated that the use of a rigid or substantially rigid backrest member 12 can permit a more even distribution of load to the body of the wheelchair user.

In some optional aspects, it is contemplated that the flexion control assembly 20 can comprise a tensioning component 22, such as, for example, a cable, a rope, a cord, a strap, or the like. In exemplary aspects, it is contemplated that the tensioning component 22 can comprise nylon, steel, parachute cord, cotton, Kevlar, or combinations thereof. It is contemplated that the tensioning component 22 can be secured to the backrest member. In these aspects, the trunk control system 100 can further comprise a spool 24 upon which the tensioning component 22 is wound. In exemplary aspects, the spool 24 can have a diameter ranging from 0.5 inches to 4 inches.

Optionally, the tensioning component 22 can comprise a Bowden cable including a cable housing 23 as is known in the art. As further disclosed herein and depicted in FIG. 5A, it is contemplated that the housing 23 can be secured to a rear portion of the wheelchair 200.

In additional aspects, the trunk control system 100 can further comprise a motor 26 that is operatively coupled to the spool 24 and configured to effect movement of the spool to selectively release or retract the tensioning component 22 on the spool 24, thereby permitting desired movement of the backrest member 12 about and between the fully retracted and fully extended positions. Optionally, in these aspects, the trunk control system 100 does not comprise an additional motor—that is, the trunk control system only includes a single motor 26. It is contemplated that the particular size of the spool can be chosen depending upon the motor 26 (and its torque output), as well as the type of tensioning component 22 (and its acceptable bend radius). In exemplary aspects, it is contemplated that the spool 24 and the motor 26 can, in combination, be strong enough to effectively lift the torso of a wheelchair user as disclosed herein. Optionally, it is contemplated that the motor 26 can be a DC motor that uses a voltage and current that can be provided by the battery of a powered wheelchair drive system as further disclosed herein.

Figure 7A:
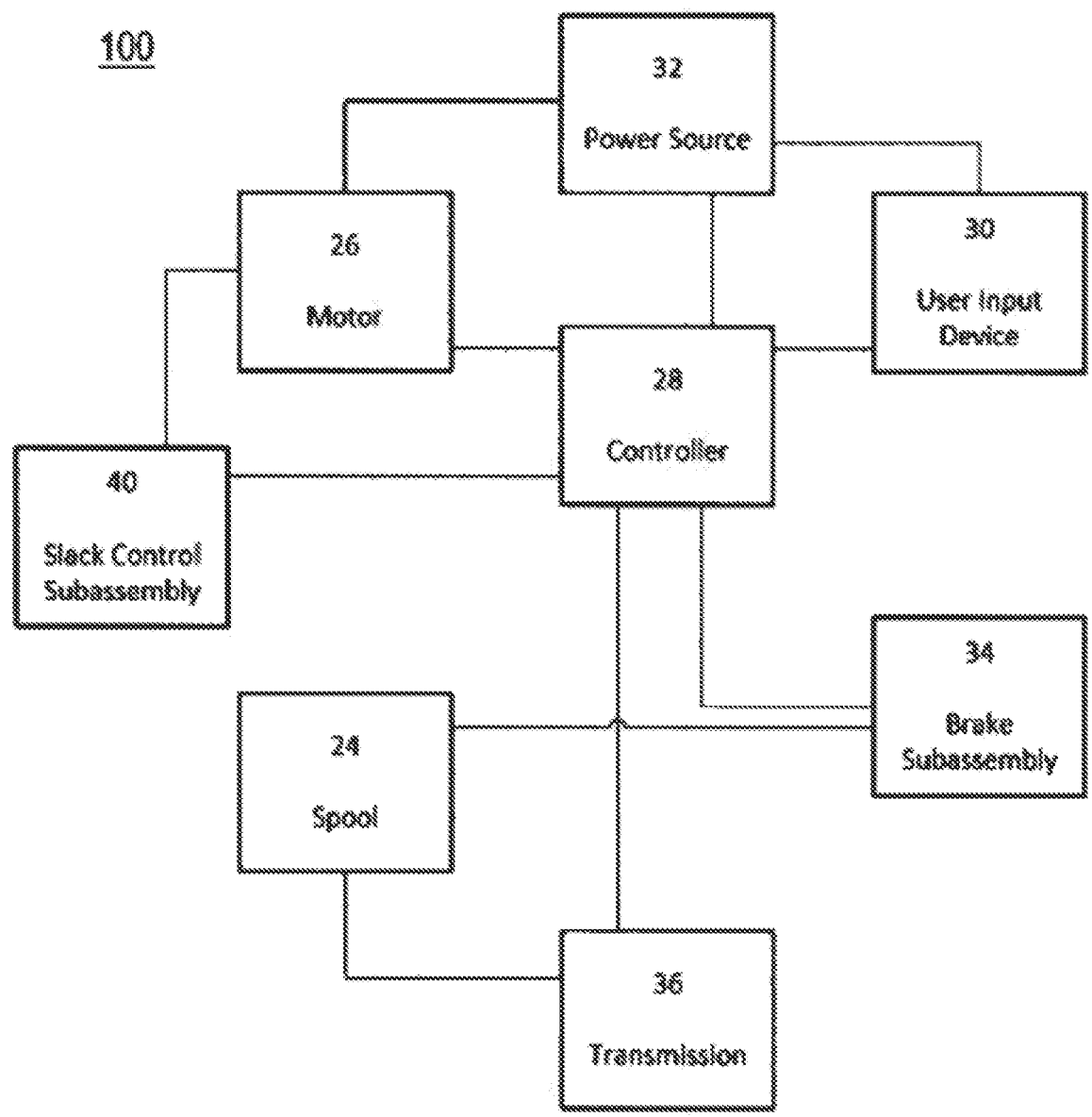
FIG. 7A is a schematic diagram depicting exemplary communication pathways between components of the flexion control assembly as disclosed herein.
Figure 7B:
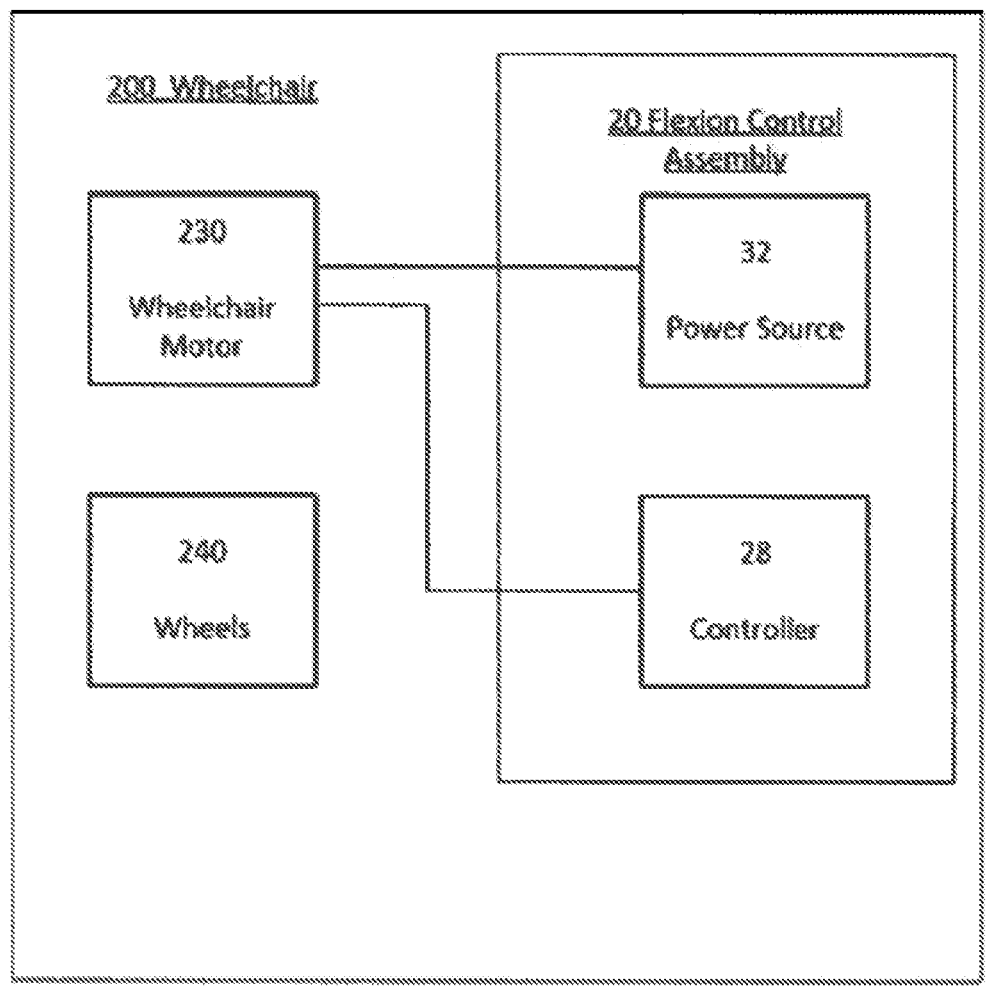
FIG. 7B is a schematic diagram depicting the use of the controller and power source of a powered wheelchair to control and power components of the flexion control assembly as disclosed herein.

In further aspects, and with reference to FIGS. 7A-7B, the trunk control system 100 can comprise a controller 28. In these aspects, the controller 28 can be operatively coupled to the motor 26. In additional aspects, the trunk control system 100 can further comprise a user input device 30. In these aspects, the user input device 30 can be communicatively coupled to the controller 28. In use, the controller 28 can be configured to receive an instruction from the user input device 30 that is indicative of a desired movement of the backrest member 12, and the controller 28 can be configured to cause the motor 26 to move the spool 24 to achieve the desired movement of the backrest member. In exemplary aspects, the controller 28 can be any conventional processing component or unit, such as for example and without limitation, a microcontroller as is known in the art. Optionally, in these aspects, the controller 28 can be provided as a component of a larger computing device, such as, for example and without limitation, a personal computer, a tablet, a smartphone, and the like.

In still further aspects, and with reference to FIGS. 7A-7B, the trunk control system 100 can further comprise a power source 32 that is configured to provide electrical power to the motor 26, the controller 28, and the user input device 30. Optionally, in these aspects, the power source 32 can comprise at least one battery, such as a rechargeable battery as is known in the art. In response to an instruction from the user input device 30 that is indicative of movement of the backrest member 12 in a direction toward the fully extended position, the controller 28 can be configured to cause the motor 26 to release the tensioning component 22 from the spool to thereby increase slack in the tensioning component and permit the desired movement of the backrest member. In response to an instruction from the user input device 30 that is indicative of movement in a direction toward the fully retracted position, the controller 28 can be configured to cause the motor 26 to retract the tensioning component 22 and pull the backrest member 12 to a desired location.

Optionally, the user input device 30 can be selected from the group consisting of: a joystick; a sip-and-puff assembly; a head switch; a chin control assembly; a voice control assembly; and combinations thereof. More generally, it is contemplated that the user input device 30 can be any conventional device for entering commands and information, including, for example and without limitation, a keyboard, pointing device (e.g., a computer mouse, remote control), a microphone, a joystick, a scanner, tactile input devices such as gloves, and other body coverings, motion sensor, and the like.

In some aspects, it can be preferable for the user input device 30 to be a joystick. For example, in one aspect, when the trunk control system 100 is provided as part of a powered wheelchair 200, it is contemplated that the user input device 30 can be a joystick, which can be used to control movement of wheels 240 of the wheelchair 200 as well as movement of the backrest member 12. Similarly, it is contemplated that the power source 32 can be used to power a wheelchair motor 230 as well as the motor 26, the controller 28, and the user input device 30 of the trunk control system 100.

Optionally, in further aspects, the flexion control assembly 20 of the trunk control system 100 can comprise a brake subassembly 34 that is configured to prevent further movement of the tensioning component 22 when the user input device 30 ceases providing instructions to the controller 28. More particularly, during use, the wheelchair user can provide movement instructions to the controller 28 (i.e., direct movement of the backrest member 12) through the user input device 30 for as long as movement of the backrest member is desired. Upon reaching a desired location for the backrest member 12, the user can stop providing movement instructions to the controller, in which case the user input device 30 is no longer receiving an input from the user. When this occurs, the brake subassembly 34 can be configured to either: (a) engage the spool 24 and/or the tensioning component 22 to prevent release or retraction of the tensioning component (i.e., serve as a physical brake on the spool) or (b) cause cessation of provision of electrical power to the motor 26 (i.e., serve as an electric brake on the motor), thereby providing stability to the backrest member 12 (and the user) after the backrest member is in a desired orientation/location.

Optionally, in further aspects, the flexion control assembly 20 of the trunk control system 100 can comprise a non-backdriveable transmission 36 that is configured to prevent release of the tensioning component 22 from the spool 24 when the user input device 30 ceases providing instructions to the controller (after completing a movement). More particularly, during use, the wheelchair user can provide movement instructions to the controller 28 (i.e., direct movement of the backrest member 12) through the user input device 30 for as long as movement of the backrest member is desired. Upon reaching a desired location for the backrest member 12, the user can stop providing movement instructions to the controller, in which case the user input device 30 is no longer receiving an input from the user. When this occurs, the transmission 36 can be configured to engage the spool to prevent further release of the tensioning component 22 from the spool 24. In exemplary aspects, the non-backdriveable transmission 36 can comprise a non-backdriveable planetary gear transmission or a non-backdriveable worm gear transmission.

In use, it is contemplated that the brake subassembly 34 or the non-backdriveable transmission 36 can reduce power consumption within the system 10 when the user is not changing trunk positions.

Figure 6A:
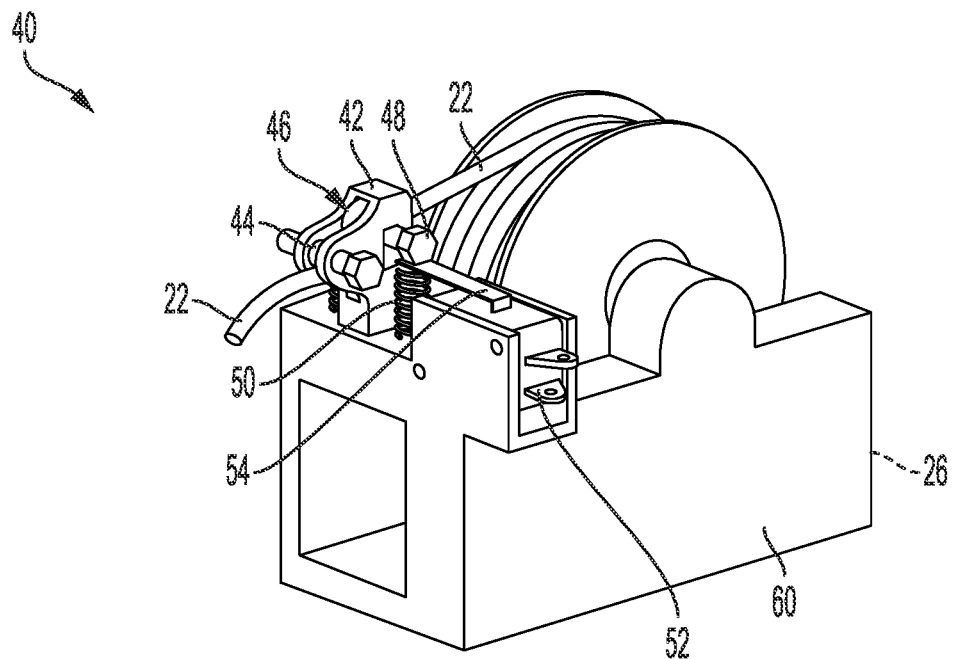
FIG. 6A is a perspective view of a slack control subassembly as disclosed herein, with an engagement element in a first position that permits slack in the tensioning component between a guide and the harness assembly.
Figure 6B:
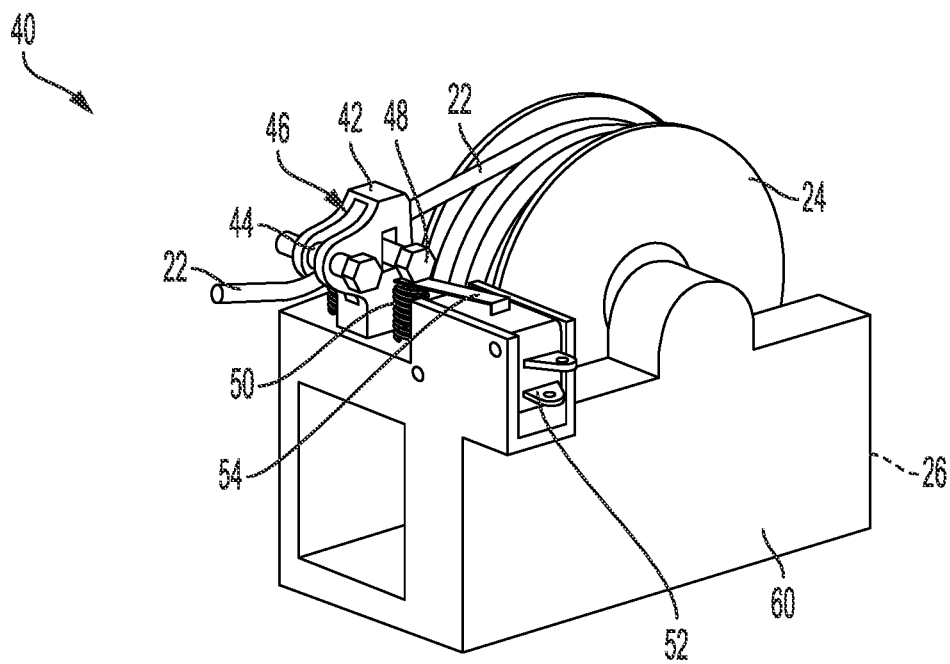
FIG. 6B is a perspective view of the slack control subassembly of FIG. 6A, with the engagement element shown in a second position that effects movement of a switch to a closed position that permits the motor to release the tensioning component from the spool.

In further aspects, and with reference to FIGS. 6A-6B, the trunk control system can further comprise a slack control subassembly 40. In these aspects, it is contemplated that the slack control subassembly 40 can have a guide 42, an engagement element 48, and at least one spring 50 (optionally, a plurality of springs). The guide 42 can be positioned between the spool 24 and the harness assembly 10. In exemplary aspects, the guide 42 can have a plurality of interior surfaces 44 that cooperate to define a channel 46 that receives the tensioning component 22 from the spool 24 and guides the tensioning component toward the harness assembly 10. The engagement element 48 can be slidably received within a portion of the channel 46 of the guide 42 and selectively moveable about and between a first position and a second position. The spring 50 can be operatively coupled to the engagement element 48 and configured to bias the engagement element to the first position. In the first position, the engagement element 48 can force the tensioning component 22 against an interior surface 44 of the guide 42 to provide tension to the tensioning component between the guide and the spool 24 but permit slack in the tensioning component between the guide and the harness assembly 10. As shown in FIGS. 6A-6B, it is contemplated that the at least one spring 50 can be positioned outside the guide 42 such that a portion of the engagement element 48 is positioned within the channel 46 of the guide 42 and a portion of the engagement element extends outside the guide 42 to engage the at least one spring. Optionally, in exemplary aspects, it is contemplated that the spring can be oriented along an axis that is perpendicular or substantially perpendicular to the orientation of the channel of the guide and/or the tensioning component 22 extending between the guide and the harness subassembly.

In further exemplary aspects, the spring 50 and the engagement element 48 can be operatively coupled to a switch 52 such that movement of the spring and the engagement element effects a corresponding movement of the switch 52. Optionally, in these aspects, the switch 52 can be a relay switch as is known in the art. In the first position, the spring 50 can effect movement of the switch 52 to an open position that prevents the motor 26 from releasing the tensioning component 22 from the spool 24. More particularly, when the switch 52 is in the open position, an open circuit is formed to prevent transmission of electrical power to the motor, thereby ensuring that the motor cannot release additional portions of the tensioning component 22 from the spool 24. Upon the application of tension sufficient to overcome the biasing of the engagement element 48 to the first position, the tensioning component 22 can be configured to displace the engagement element to the second position. In the second position, the engagement element 48 can effect movement of the switch 52 to a closed position that permits the motor to release of the tensioning component 22 from the spool. More particularly, when the switch 52 is in the closed position, a closed circuit is formed to transmit electrical power to the motor 26, thereby allowing the motor to release additional portions of the tensioning component 22 from the spool 24. In further aspects, the switch 52 can be operatively coupled to the spring 50 and the engagement element 48 by an arm 54 that extends between the switch and the spring. Alternatively, it is contemplated that the switch 52 can be operatively coupled to the spring 50 and the engagement element 48 using a proximity sensor and/or a pressure sensor that provides an indication of the location of the spring 50 and/or engagement element 48. In these alternative aspects, it is contemplated that the switch 52 can comprise a pressure switch or a proximity switch that can be configured to provide current and electrical power to the motor 26 in response to a particular pressure or proximity threshold.

Optionally, as shown in FIGS. 6A-6B, the trunk control system 100 can comprise a housing 60 that receives or supports the spool, the motor, and the slack control subassembly. In one exemplary configuration, it is contemplated that the housing 60 can be secured or incorporated into the seat 210 (e.g., the seat back) of the wheelchair 200.

In use, it is contemplated that the slack control subassembly 40 can keep slack in the tensioning component 22 away from the spool during use of the trunk control system 10. It is contemplated that the slack control subassembly 40 can be used in conjunction with, and in addition to, the controller 28. If the user is trying to release the tensioning component and the switch is in the closed position (indicative of tension in the line), then the motor will be permitted to release additional length of the tensioning component. However, if the user is trying to release the tensioning component 22 and the switch is in the open position (indicative of slack in the line), then the motor will not be permitted to release additional length of the tensioning component. This ensures that the slack is removed before the motor effects movement of the spool, thereby minimizing the risk of the slack becoming entangled with the spool or motor.

Although the embodiments depicted in FIGS. 1A-7B utilize a powered spool, it is contemplated that the spool can instead comprise a spring-loaded spool having a releasable brake. The spring-loaded spool can be configured to retract the tensioning component 22 when the brake is released to permit backward movement. The spool can be further configured to be overpowered by gravity of the trunk or by forward pulling force from the user to permit forward movement, thereby permitting full adjustment of trunk positions. In these aspects, the spring-loaded spool can be locked into selected positions by the user, allowing bimanual tasks to occur at set positions. When finished, the user can release the brake on the spool, and pull themselves back to a vertical position (or other fully retracted position) with their arms, while the spring-loaded spool retracts the tensioning component. Once retracted fully, the spool can be locked again to hold the user in the fully retracted (e.g., vertical) position.

Although the embodiments depicted in FIGS. 1A-6B reflect the use of ropes, cables, or cords, it is contemplated that spring-loaded strap systems can also be used as the tensioning component. Spring-loaded strap systems, such as those used in automobile seat belts, can be used to create a passive (spring-loaded) system as disclosed above with respect to the spring-loaded spool. Alternatively, it is contemplated that motors can be used to create powered systems.

Further, it is contemplated that linear motion may be used to effect retraction and release of the tensioning component 22 instead of rotary movement on a spool. For example, a releasable gas spring can be connected to one end of the tensioning component 22 to allow controlled lengthening, with a braking effect when the user is at the preferred trunk flexion position. It is contemplated that other manually driven spools can be used without departing from the spirit of this disclosure. For example, it is contemplated that a crank mechanism can be rotated to allow the user to control trunk flexion position.

As further described herein, it is contemplated that the disclosed trunk control system 100 can be incorporated into a wheelchair 200, such as a powered wheelchair.

In exemplary aspects, as shown in FIGS. 1A-5B, the wheelchair 200 can comprise a seat 210 having a back support portion 215, and the flexion control assembly 20 of the trunk control system 100 can comprise a tensioning component 22 that extends through the back support portion. As shown in FIG. 5A, the housing 23 (e.g., cable housing) can receive the tensioning component 22 after it passes through the back support portion 215 (moving away from the harness assembly 10).

As shown in FIG. 7B, the wheelchair 200 can comprise a wheelchair motor 230 and a plurality of wheels 240. In use, the wheelchair motor 230 is configured to drive movement of the plurality of wheels 240. In exemplary aspects, the power source 32 can be configured to provide electrical power to the wheelchair motor 230, and the motor 26, the controller 28, and the user input device 30 of the trunk control system 100. In further exemplary aspects, the controller 28 of the trunk control system 100 can be operatively coupled to the wheelchair motor 230 and further configured to cause the wheelchair motor to effect selected movements of the plurality of wheels 240 of the wheelchair 200. In these aspects, the user input device 30 of the trunk control system 100 can be configured to provide instructions indicative of the selected movements of the plurality of wheels 240 of the wheelchair 200. Optionally, it is contemplated that the user input device 30 of the trunk control system 100 can be a joystick (such as the type of joystick conventionally provided on a powered wheelchair), or can be controlled by a knee switch, or by a sip-and-puff control approach used to operate wheelchairs and other assistive technologies.

Optionally, it is contemplated the trunk control system 100 disclosed herein can be retrofit to an electric (powered) wheelchair as is known in the art.

Optionally, it is contemplated that the trunk control system 100 can be provided with a wheelchair back support as a wheelchair back assembly that is configured to be secured to the wheelchair 200. In these aspects, it is contemplated that the harness assembly of the trunk control system 100 can be configured for movement relative to the wheelchair back support. For example, it is contemplated that the wheelchair back assembly can be provided with the flexion control assembly coupled to or integrated into the wheel chair back support. It is further contemplated that power to the trunk control system can be independent of the wheelchair 200 or connected into the battery of the wheelchair.

Exemplary Aspects

In view of the described products, systems, and methods and variations thereof, herein below are described certain more particularly described aspects of the invention. These particularly recited aspects should not however be interpreted to have any limiting effect on any different claims containing different or more general teachings described herein, or that the "particular" aspects are somehow limited in some way other than the inherent meanings of the language literally used therein.

Aspect 1: A trunk control system comprising: a harness assembly having: a backrest member configured to be moveably coupled to a wheelchair, wherein the backrest member is selectively moveable about and between a fully retracted position and a fully extended position; and a harness secured to the backrest member, wherein the harness cooperates with the backrest member to define a receiving space for receiving at least a portion of a torso of a wheelchair user; and a flexion control assembly coupled to the backrest member of the harness assembly, wherein the flexion control assembly is configured to selectively permit or restrict movement of the backrest member about and between the fully retracted position and the fully extended position.

Aspect 2: The trunk control system of aspect 1, wherein the flexion control assembly comprises a tensioning component, and wherein the tensioning component comprises a cable, a rope, a cord, a cable, or combinations thereof.

Aspect 3: The trunk control system of aspect 2, further comprising a spool, wherein the tensioning component is secured to the backrest member and wound around the spool.

Aspect 4: The trunk control system of aspect 3, further comprising a motor, wherein the motor is operatively coupled to the spool and configured to effect movement of the spool to selectively release or retract the tensioning component on the spool.

Aspect 5: The trunk control system of aspect 4, wherein the trunk control system does not comprise an additional motor.

Aspect 6: The trunk control system of aspect 4 or aspect 5, further comprising a controller, wherein the controller is operatively coupled to the motor.

Aspect 7: The trunk control system of aspect 6, further comprising a user input device, wherein the user input device is communicatively coupled to the controller, wherein the controller is configured to receive an instruction from the user input device that is indicative of a desired movement of the backrest member, and wherein the controller is configured to cause the motor to move the spool to achieve the desired movement of the backrest member.

Aspect 8: The trunk control system of aspect 7, wherein the user input device is selected from the group consisting of: a joystick; a sip-and-puff assembly; a head switch; a chin control assembly; a voice control assembly; myoelectric, eye-gaze, tilt-switch; and combinations thereof.

Aspect 9: The trunk control system of aspect 7, wherein the user input device is a joystick.

Aspect 10: The trunk control system of any one of claims 7-9, further comprising a power source that is configured to provide electrical power to the motor, the controller, and the user input device.

Aspect 11: The trunk control system of any one of aspects 7-10, wherein in response to an instruction from the user input device that is indicative of movement in a direction toward the fully extended position, the controller is configured to cause the motor to increase slack in the tensioning component.

Aspect 12: The trunk control system of aspect 11, wherein the flexion control assembly comprises a brake subassembly that is configured to prevent further movement of the tensioning component when the user input device ceases providing instructions to the controller.

Aspect 13: The trunk control system of aspect 12, wherein in response to an instruction from the user input device that is indicative of movement in a direction toward the fully retracted position, the controller is configured to cause the motor to retract the tensioning component.

Aspect 14: The trunk control system of aspect 11, wherein the flexion control assembly comprises a non-backdriveable transmission that is configured to prevent release of the tensioning component from the spool when the user input device ceases providing instructions to the controller.

Aspect 15: The trunk control system of aspect 14, wherein in response to an instruction from the user input device that is indicative of movement in a direction toward the fully retracted position, the controller is configured to cause the motor to retract the tensioning component.

Aspect 16: The trunk control system of any one of aspects 7-15, wherein the further comprises a slack control subassembly, the slack control subassembly having: a guide positioned between the spool and the harness assembly, wherein the guide has a plurality of interior surfaces that cooperate to define a channel that receives the tensioning component from the spool and guides the tensioning component toward the harness assembly; an engagement element slidably received within the channel of the guide and selectively moveable about and between a first position and a second position; a spring operatively coupled to the engagement element and configured to bias the engagement element to the first position, wherein in the first position, the engagement element forces the tensioning component against an interior surface of the guide to provide tension to the tensioning component between the guide and the spool but permit slack in the tensioning component between the guide and the harness assembly.

Aspect 17: The trunk control system of aspect 16, wherein the spring and the engagement element are operatively coupled to a switch such that movement of the spring and the engagement element effects a corresponding movement of the switch, wherein in the first position, the spring effects movement of the switch to an open position that prevents the motor from releasing the tensioning component from the spool.

Aspect 18: The trunk control system of aspect 17, wherein upon the application of tension sufficient to overcome the biasing of the engagement element to the first position, the tensioning component is configured to displace the engagement element to the second position, and wherein in the second position, the engagement element effects movement of the switch to a closed position that permits the motor to release of the tensioning component from the spool.

Aspect 19: The trunk control system of aspect 18, wherein the switch is operatively coupled to the spring and the engagement element by an arm that extends between the switch and the spring.

Aspect 20: The trunk control system of any one of aspects 16-19, further comprising a housing, wherein the housing receives or supports the spool, the motor, and the slack control subassembly.

Aspect 21: The trunk control system of any one of aspects 2-20, wherein the tensioning component of the flexion control assembly comprises a Bowden cable.

Aspect 22: The trunk control system of any one of the preceding aspects, wherein the backrest member comprises a rigid structure.

Aspect 23: The trunk control system of any one of the preceding aspects, wherein the harness of the harness assembly comprises first and second shoulder straps and a releasable horizontal strap that is configured to extend across a chest of the wheelchair user in between the first and second shoulder straps.

Aspect 24: The trunk control system of aspect 1, wherein the flexion control assembly comprises at least one strap.

Aspect 25: The trunk control system of aspect 3, wherein the spool is spring-loaded.

Aspect 26: A wheelchair comprising the trunk control system of any one of aspects 1-25.

Aspect 27: The wheelchair of aspect 26, wherein the wheelchair comprises a seat having a back support portion, and wherein the flexion control assembly of the trunk control system comprises a tensioning component that extends through the back support support portion.

Aspect 28: The wheelchair of aspect 27, further comprising a cable housing secured to the back support portion of the housing, wherein the tensioning component comprises a Bowden cable that extends through the cable housing.

Aspect 29: The wheelchair of any one of aspects 26-28, further comprising a wheelchair motor and a plurality of wheels, wherein the wheelchair motor is configured to drive movement of the plurality of wheels, wherein the flexion control assembly of the trunk control system comprises a tensioning component, and wherein the trunk control system comprises: a spool, wherein the tensioning component is secured to the backrest member and wound around the spool; a motor, wherein the motor is operatively coupled to the spool and configured to effect movement of the spool to selectively release or retract the tensioning component on the spool; a controller, wherein the controller is operatively coupled to the motor; a user input device, wherein the user input device is communicatively coupled to the controller, wherein the controller is configured to receive an instruction from the user input device that is indicative of a desired movement of the backrest member, and wherein the controller is configured to cause the motor to move the spool to achieve the desired movement of the backrest member; and a power source that is configured to provide electrical power to the wheelchair motor, and the motor, the controller, and the user input device of the trunk control system.

Aspect 30: The wheelchair of aspect 29, wherein the controller of the trunk control system is operatively coupled to the wheelchair motor and further configured to cause the wheelchair motor to effect selected movements of the plurality of wheels of the wheelchair, and wherein the user input device of the trunk control system is configured to provide instructions indicative of the selected movements of the plurality of wheels of the wheelchair.

Aspect 31: The wheelchair of aspect 30, wherein the user input device of the trunk control system is a joystick.

Aspect 32: A method of using the wheelchair of any one of aspects 26-31.

Aspect 33: A wheelchair back assembly comprising: the trunk control system of any one of aspects 1-25; and a wheelchair back support that is configured to be secured to a wheelchair, wherein the harness assembly of the trunk control system is configured for movement relative to the wheelchair back support.

Aspect 34: The wheelchair back assembly of aspect 33, wherein the flexion control assembly of the trunk control system is coupled to the wheelchair back support.

Aspect 35: A trunk control system comprising: a harness configured to be worn by a wheelchair user, the harness having a posterior portion; one or more tensioning components attached to the posterior portion of the harness and configured to be selectively released or retracted to adjust a position of the harness; means for controlling a path of the one or more tensioning components; means for releasing or retracting the one or more tensioning components; and means for controlling the release or retraction of the one or more tensioning components.

Although the foregoing invention has been described in some detail by way of illustration and example for purposes of clarity of understanding, certain changes and modifications may be practiced within the scope of the appended claims.

What is claimed is:

1. A trunk control system comprising:
a harness assembly having:
a backrest member configured to be moveably coupled to a wheelchair, wherein the backrest member is selectively moveable about and between a fully retracted position and a fully extended position; and
a harness secured to the backrest member, wherein the harness cooperates with the backrest member to define a receiving space for receiving at least a portion of a torso of a wheelchair user; and
a flexion control assembly coupled to the backrest member of the harness assembly, wherein the flexion control assembly is configured to selectively permit or restrict movement of the backrest member about and between the fully retracted position and the fully extended position.

2. The trunk control system of claim 1, wherein the flexion control assembly comprises a tensioning component, wherein the tensioning component comprises a rope, a cable, a cord, a strap, or combinations thereof.

3. The trunk control system of 2, further comprising a spool, wherein the tensioning component is secured to the backrest member and wound around the spool.

4. The trunk control system of claim 3, wherein the spool is spring-loaded.

5. The trunk control system of claim 3, further comprising a motor, wherein the motor is operatively coupled to the spool and configured to effect movement of the spool to selectively release or retract the tensioning component on the spool.

6. The trunk control system of claim 5, wherein the trunk control system does not comprise an additional motor.

7. The trunk control system of claim 5, further comprising a controller, wherein the controller is operatively coupled to the motor.

8. The trunk control system of claim 7, further comprising a user input device, wherein the user input device is communicatively coupled to the controller, wherein the controller is configured to receive an instruction from the user input device that is indicative of a desired movement of the backrest member, and wherein the controller is configured to cause the motor to move the spool to achieve the desired movement of the backrest member.

9. The trunk control system of claim 8, wherein the user input device is selected from the group consisting of: a joystick; a sip-and-puff assembly; a head switch; a chin control assembly; a voice control assembly; a myoelectric, eye-gaze, tilt-switch; and combinations thereof.

10. The trunk control system of claim 8, wherein the user input device is a joystick.

11. The trunk control system of claim 8, further comprising a power source that is configured to provide electrical power to the motor, the controller, and the user input device.

12. The trunk control system of claim 8, wherein in response to an instruction from the user input device that is indicative of movement in a direction toward the fully extended position, the controller is configured to cause the motor to increase slack in the tensioning component.

13. The trunk control system of claim 12, wherein the flexion control assembly comprises a brake subassembly that is configured to prevent further movement of the tensioning component when the user input device ceases providing instructions to the controller.

14. The trunk control system of claim 13, wherein in response to an instruction from the user input device that is indicative of movement in a direction toward the fully retracted position, the controller is configured to cause the motor to retract the tensioning component.

15. The trunk control system of claim 12, wherein the flexion control assembly comprises a non-backdriveable transmission that is configured to prevent release of the tensioning component from the spool when the user input device ceases providing instructions to the controller.

16. The trunk control system of claim 15, wherein in response to an instruction from the user input device that is indicative of movement in a direction toward the fully retracted position, the controller is configured to cause the motor to retract the tensioning component.

17. The trunk control system of claim 8, wherein the further comprises a slack control subassembly, the slack control subassembly having:
   a guide positioned between the spool and the harness assembly, wherein the guide has a plurality of interior surfaces that cooperate to define a channel that receives the tensioning component from the spool and guides the tensioning component toward the harness assembly;
   a engagement element slidably received within the channel of the guide and selectively moveable about and between a first position and a second position;
   a spring operatively coupled to the engagement element and configured to bias the engagement element to the first position,
   wherein in the first position, the engagement element forces the tensioning component against an interior surface of the guide to provide tension to the tensioning component between the guide and the spool but permit slack in the tensioning component between the guide and the harness assembly.

18. The trunk control system of claim 17, wherein the spring and the engagement element are operatively coupled to a switch such that movement of the spring and the engagement element effects a corresponding movement of the switch, wherein in the first position, the spring effects movement of the switch to an open position that prevents the motor from releasing the tensioning component from the spool.

19. The trunk control system of claim 18, wherein upon the application of tension sufficient to overcome the biasing of the engagement element to the first position, the tensioning component is configured to displace the engagement element to the second position, and wherein in the second position, the engagement element effects movement of the switch to a closed position that permits the motor to release of the tensioning component from the spool.

20. The trunk control system of claim 19, wherein the switch is operatively coupled to the spring and the engagement element by an arm that extends between the switch and the spring.

21. The trunk control system of claim 17, further comprising a housing, wherein the housing receives or supports the spool, the motor, and the slack control subassembly.

22. The trunk control system of claim 2, wherein the tensioning component of the flexion control assembly comprises a Bowden cable.

23. The trunk control system of claim 1, wherein the backrest member comprises a rigid structure.

24. The trunk control system of claim 1, wherein the harness of the harness assembly comprises first and second shoulder straps and a releasable horizontal strap that is configured to extend across a chest of the wheelchair user in between the first and second shoulder straps.

25. The trunk control system of claim 1, wherein the flexion control assembly comprises at least one strap.

26. A wheelchair comprising:
   a trunk control system comprising:
      a harness assembly, the harness assembly having:
         a backrest member configured to be moveably coupled to a wheelchair, wherein the backrest member is selectively moveable about and between a fully retracted position and a fully extended position; and
         a harness secured to the backrest member, wherein the harness cooperates with the backrest member to define a receiving space for receiving at least a portion of a torso of a wheelchair user; and
      a flexion control assembly coupled to the backrest member of the harness assembly, wherein the flexion control assembly is configured to selectively permit or restrict movement of the backrest member about and between the fully retracted position and the fully extended position; and
   a seat having a back support portion,
   wherein the flexion control assembly of the trunk control system comprises a tensioning component that extends through the back support portion.

27. The wheelchair of claim 26, further comprising a cable housing secured to the back support portion of the housing, wherein the tensioning component comprises a Bowden cable that extends through the cable housing.

28. The wheelchair of claim 26, further comprising a wheelchair motor and a plurality of wheels, wherein the wheelchair motor is configured to drive movement of the plurality of wheels, wherein the flexion control assembly of the trunk control system comprises a tensioning component, and wherein the trunk control system comprises:
   a spool, wherein the tensioning component is secured to the backrest member and wound around the spool;
   a motor, wherein the motor is operatively coupled to the spool and configured to effect movement of the spool to selectively release or retract the tensioning component on the spool;
   a controller, wherein the controller is operatively coupled to the motor;
   a user input device, wherein the user input device is communicatively coupled to the controller, wherein the controller is configured to receive an instruction from the user input device that is indicative of a desired movement of the backrest member, and wherein the controller is configured to cause the motor to move the spool to achieve the desired movement of the backrest member; and
   a power source that is configured to provide electrical power to the wheelchair motor, and the motor, the controller, and the user input device of the trunk control system.

29. The wheelchair of claim 28, wherein the controller of the trunk control system is operatively coupled to the wheelchair motor and further configured to cause the wheelchair motor to effect selected movements of the plurality of wheels of the wheelchair, and wherein the user input device of the trunk control system is configured to provide instructions indicative of the selected movements of the plurality of wheels of the wheelchair.

30. The wheelchair of claim 29, wherein the user input device of the trunk control system is a joystick.

31. A wheelchair back assembly comprising:
a trunk control system comprising:
  a harness assembly, the harness assembly having:
    a backrest member configured to be moveably coupled to a wheelchair, wherein the backrest member is selectively moveable about and between a fully retracted position and a fully extended position; and
    a harness secured to the backrest member, wherein the harness cooperates with the backrest member to define a receiving space for receiving at least a portion of a torso of a wheelchair user; and
  a flexion control assembly coupled to the backrest member of the harness assembly, wherein the flexion control assembly is configured to selectively permit or restrict movement of the backrest member about and between the fully retracted position and the fully extended position; and
a wheelchair back support that is configured to be secured to a wheelchair, wherein the harness assembly of the trunk control system is configured for movement relative to the wheelchair back support.

32. The wheelchair back assembly of claim 31, wherein the flexion control assembly of the trunk control system is coupled to the wheelchair back support.

\* \* \* \* \*